United States Patent [19]

Mancosu et al.

[11] Patent Number: 5,239,184

[45] Date of Patent: Aug. 24, 1993

[54] PROCESS AND MACHINE FOR SPOTTING SUPERFICIAL DEFECTS ON LAYERS AND/OR SLEEVES OF ELASTOMERIC MATERIAL

[75] Inventors: Federico Mancosu, Milan; Simone Schiatti, Desio; Roberto Zavaglio, Milan, all of Italy

[73] Assignee: Pirelli Produtti Diversificati S.p.A., Italy

[21] Appl. No.: 811,237

[22] Filed: Dec. 20, 1991

[30] Foreign Application Priority Data

Dec. 21, 1990 [IT] Italy ................................ 22505 A/90

[51] Int. Cl.⁵ ............................................ G01N 21/88
[52] U.S. Cl. ................................... 250/562; 350/430
[58] Field of Search ................. 250/562, 572, 223 R, 250/223 B, 208.1; 364/470, 471, 472, 473, 575, 581, 551.01; 382/8, 27; 356/430, 238, 237

[56] References Cited

U.S. PATENT DOCUMENTS

| | | | |
|---|---|---|---|
| 4,665,317 | 5/1987 | Ferriere | 356/430 |
| 4,974,261 | 11/1990 | Nakahara et al. | 356/237 |
| 5,068,799 | 11/1991 | Jarrell, Jr. | 356/238 |
| 5,118,195 | 6/1992 | Dobbie | 356/430 |

FOREIGN PATENT DOCUMENTS 0048568 3/1982 European Pat. Off. .
2592486 7/1987 France .

OTHER PUBLICATIONS

Iron and Steel Engineer, vol. 67, No. 5, May 1990, Pittsburgh US, pp. 26–29; Morris Ho: "Surface Inspection System with Defect Classification" p. 29.

*Primary Examiner*—David C. Nelms
*Assistant Examiner*—K. Shami
*Attorney, Agent, or Firm*—Stevens, Davis, Miller & Mosher

[57] ABSTRACT

A sleeve (2) of elastomeric material is operationally mounted on support rollers (5, 6) which can be operated to rotate the sleeve. At least one or more television camera (15) shoots the surface (2a) of the sleeve (2) which is illuminated with light at a low angle. The superficial appearance of the sleeve (2) is recorded in the form of images, each divided into a plurality of pixels (P) distributed in an orderly fashion. The values of luminosity of the individual pixels (P) are recorded and processed to highlight those pixels wherein due to superficial irregularities (C) on the sleeve (2), a variation is detected of the light reflected by the surface (2a) of the sleeve itself. On the basis of the position occupied by the highlighted pixels (P) it is possible to go back to the position of the superficial defects (C) along the extension of the sleeve (2).

21 Claims, 3 Drawing Sheets

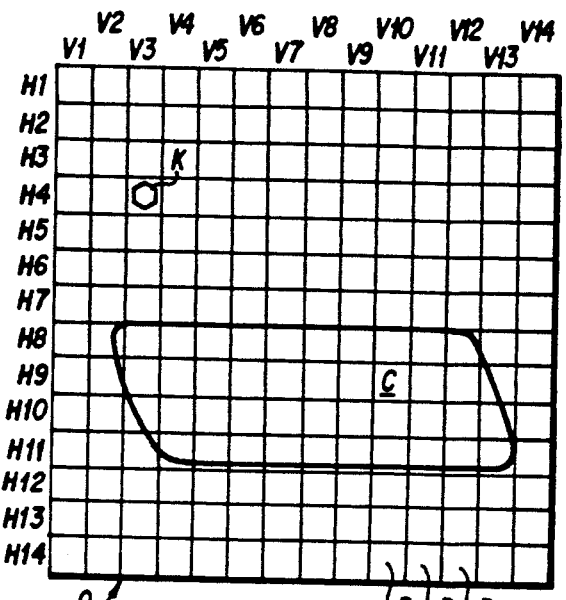
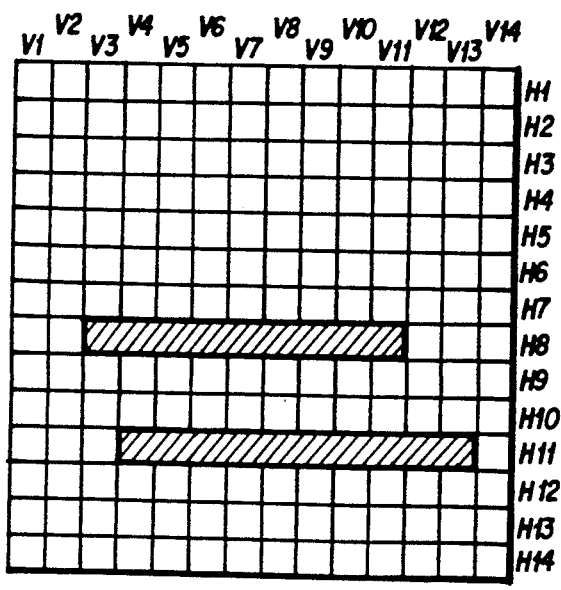

FIG. 6a
| 0 | 0 | 0 | H7 |
|---|---|---|---|
| 0 | 0 | 0 | H8 |
| 0 | 0 | 0 | H9 |
V8 V9 V10
FIG. 6
| 1 | 0 | -1 |
|---|---|---|
| 1 | 0 | -1 |
| 1 | 0 | -1 |
FIG. 6b
| H3 | 36 | 0 | 36 |
|---|---|---|---|
| H4 | 54 | 0 | 54 |
| H5 | 36 | 0 | 36 |
V2 V3 V4
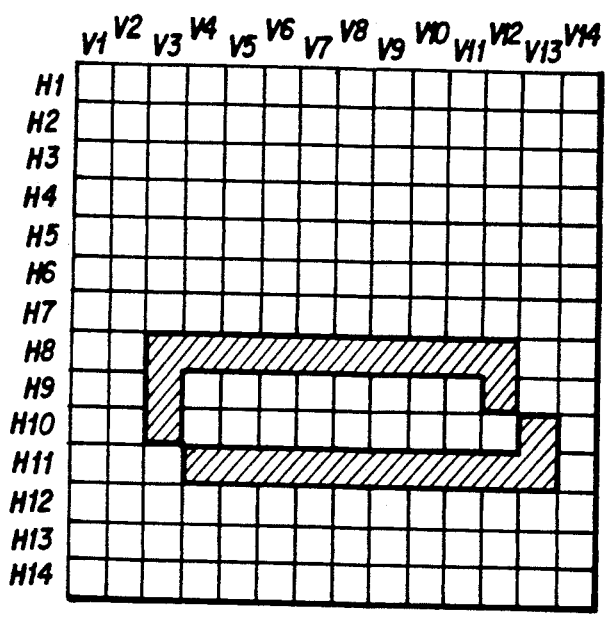
FIG. 6c
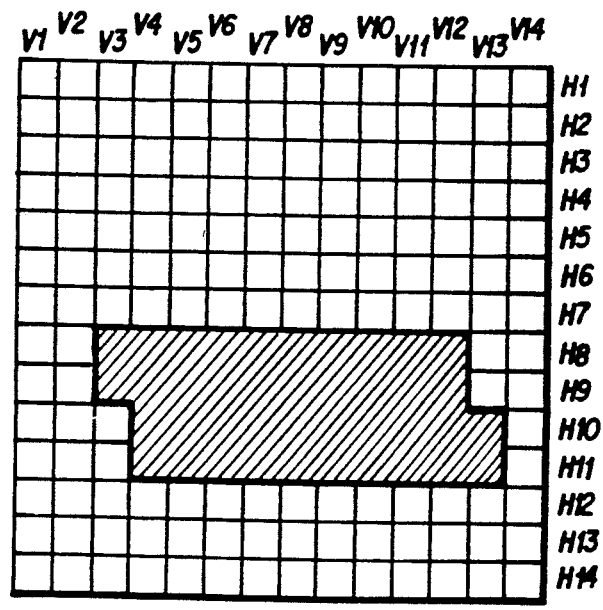
FIG. 7

PROCESS AND MACHINE FOR SPOTTING SUPERFICIAL DEFECTS ON LAYERS AND/OR SLEEVES OF ELASTOMERIC MATERIAL

CROSS REFERENCE TO RELATED APPLICATIONS

Copending U.S. patent application Ser. No. 07/792,876, filed on even date herewith and corresponding to:

Italian Application 22 121 A/90, filed Nov. 21, 1990 for PROCESS AND APPARATUS TO APPLY IDENTIFICATION INSCRIPTIONS ON SLEEVES MADE OF ELASTOMERIC MATERIAL IN THE MANUFACTURE OF DRIVING BELTS.

Copending U.S. patent application Ser. No. 07/793,731, filed on even date herewith and corresponding to:

Italian Application 22 123 A/90, filed Nov. 21, 1990 for PROCESS AND APPARATUS FOR HANDLING DRIVING BELTS IN AN AUTOMATED MANNER.

Copending U.S. patent application Ser. No. 07/793,840, filed on even date herewith and corresponding to:

Italian Application 22 124 A/90, filed Nov. 21, 1990 for MACHINE AND PROCESS FOR COILING AND WINDING TUBULAR SLEEVES OF ELASTOMERIC MATERIAL INCORPORATING REINFORCING FIBERS.

Copending U.S. patent application Ser. No. 07/793,732 filed on even date herewith and corresponding to:

Italian Application 22 125 A/90, filed Nov. 21, 1990 for PROCESS AND APPARATUS TO INSPECTING JUNCTIONS IN SLEEVE LINING FABRICS FOR THE MANUFACTURE OF TOOTHED BELTS.

Copending U.S. patent application Ser. No. 07/793,733, filed on even date herewith and corresponding to:

Italian Application 22 126 A/90, filed Nov. 21, 1990 for PROCESS AND APPARATUS TO IDENTIFY THE PRESENCE OF STRUCTURAL CAVITIES IN SLEEVES FOR THE MANUFACTURE OF DRIVING BELTS.

Copending U.S. patent application Ser. No. 07/792,880, filed on even date herewith and corresponding to:

Italian Application 22 127 A/90, filed Nov. 21, 1990 for PROCESS AND AUTOMATIC INSTALLATION FOR THE CONTROL OF THE QUALITY AND OF THE PRODUCTION OF TRANSMISSION BELTS.

Copending U.S. patent application Ser. No. 07/793,729, filed on even date herewith and corresponding to:

Italian Application 22 128 A/90, filed Nov. 21, 1990 for A PROCESS AND APPARATUS FOR INSPECTING THE GEOMETRICAL CONFIGURATION OF TOOTHED DRIVING ELEMENTS.

The disclosure of each of the above identified U.S. and Italian Applications are hereby incorporated by reference.

BACKGROUND OF THE INVENTION

The present invention relates to a process and to a machine for spotting superficial defects on layers and in particular on sleeves of elastomeric material.

In the embodiment described hereinafter, the subject process and the subject machine are ready to be used in the qualitative verification sleeves having an axially tubular body that after passing quality control test, will be cut at a plurality of axially spaced points so as to produce a plurality of transmission belts, and more accurately toothed belts.

This does not, however, exclude the possibility of the use of the invention for spotting superficial defects on sleeves for belts of other types, such as, say, trapezoid-shaped or flat or grooved belts, or for spotting superficial defects on sleeves or other products of elastomeric material of a different type, such as, say, flexible hoses and rubber-coated panels.

As is known, in the production of transmission belts in general, there is first provided an axially elongated tubular sleeve, which is ready to be cut along several axially equidistantly spaced circumferential lines so as to obtain the separation of the individual belts.

This sleeve is made by winding in succession, on a suitable cylindrical matrix, one or more layers of elastomeric material combined with at least one layer of inextensible cords, circumferentially wound onto the matrix itself.

After these winding operations, the semi-finished product is coated with a protective sheet of paper or such like, to be subsequently subjected to a curing operation in an autoclave.

During the course of the curing operation the semi-finished product, which is first encased in a rubber chamber or coating sheath, is subjected to a combined action of heat and centripetal compression for example by steam under pressure, applied to the outside of the rubber sheath, forcing the rubber into the interstices of the reinforcement layers and takes the shape of teeth on the exterior surface of the matrix.

At the end of the curing operation the tubular sleeve obtained, previously removed from the autoclave and from the chamber or rubber sheath, must be subjected to a so-called "rasping" operation to remove the protective sheet of paper which was applied earlier so as to avoid, during the curing operation, that the elastomeric material in the uncured state might adhere to the rubber sheath. The rasping operation has the further object of evening out the sleeve's outer surface.

Before proceeding with the circumferential cutting operations to obtain the individual belts, it is important that the sleeve be subjected to some qualitative checks, to verify the possible presence of structural defects in the same.

One of these checks consists of identifying the possible presence of superficial irregularities which can be constituted, say, by fragments of paper not removed during the rasping step.

Other types of irregularities which can be found, are cuts, cracks or grooves localized on the surface of the sleeve, due, for example, to the seepage of steam or to other drawbacks which have occurred during the curing operation and/or during the course of processes prior to it.

The surface of the sleeve can also have local swellings due to the seepage of gases from inside the elastomeric material, or, in this case again, to the seepage of steam during the curing operation.

Lastly, it can occur that at certain points on the surface of the sleeve there are irregularities due to the presence of junction knots made on the inextensible cords during the course of the previous winding stage.

The methods currently in use to identify all these possible irregularities are substantially based on the visual examination of the surface of the sleeve on the part of an operator. It is evident, that the outcomes of such a check are entirely subjective, since they depend on the ability of the operator and on the attention he or she devotes to the execution of the check.

SUMMARY OF THE INVENTION

The Applicant has found that in order to execute an objective and reliable check of the layer or of a sleeve of elastomeric material it is possible to use a method based on the processing and interpretation of images taken by means of television cameras, so as to spot the presence of superficial imperfections on the basis of the changes in the reflection of light on the surface of the sleeve in the different areas thereof.

The present invention provides for a process for spotting superficial defects on layers of elastomeric material, characterized in that it comprises the following steps:

operationally mounting said layer on a support means;

illuminating the surface of the layer with light at a low angle;

shooting the surface of the layer with at least one television camera to obtain at least one image of said surface, dividing that image into a plurality of pixels distributed in an orderly fashion in horizontal rows and vertical rows intersecting one another;

reading the value of luminosity of the image at each pixel;

assigning to each pixel a first fictitious value of luminosity corresponding to the difference between the values of luminosity of at least two pixels contiguous with it, belonging to the horizontal rows contiguous with the horizontal row to which the pixel to which the first fictitious value is attributed respectively belongs;

discriminating the pixels whose first fictitious value is above a pre-set threshold level, from the pixels whose first fictitious value is below the threshold level;

assigning to each pixel a second fictitious value of luminosity, corresponding to the difference between the values of luminosity of at least two pixels contiguous with it, belonging to vertical rows contiguous with the vertical row to which the pixel to which the second fictitious value is attributed respectively belongs;

discriminating the pixels whose second fictitious value is above the pre-set threshold level, from the pixels whose second fictitious value is below said threshold level;

spotting the position of the superficial defects of the layer, on the basis of at least the vertical rows to which each of the pixels belongs wherein at least one of said fictitious values is above the threshold level.

Preferentially, with the object of excluding any chance that possible crystals or such like with a high degree of reflection be recognized as defects, the process is characterized in that prior to the assignment of the first fictitious value, the assignment is made to each of said pixels, of a value of weighted average of luminosity, corresponding to the sum of the values of luminosity of the same pixel and of the pixels adjacent to it, divided by the number of values of luminosity added together.

In a particular preferential embodiment of the invention a process is provided for the manufacture of transmission belts comprising an annular body of elastomeric material incorporating at least one layer of longitudinal reinforcing cords arranged side by side to one another, said process comprising the steps of:

winding in succession on a cylindrical matrix one or more layers of elastomeric material combined with at least one layer of inextensible cords, wound circumferentially onto said matrix;

coating the final layer of the sleeve obtained with a sheet of paper or such like;

engaging over the layer of paper coating a rubber sheath and curing the sleeve by exerting a combined action of heating and centripetal pressure on the part of fluid under pressure, applied on the outside of the rubber sheath, as well as inside the matrix;

extracting the sleeve from the sheath at the end of the curing operation;

rasping the external surface of the sleeve to remove said sheet of paper and evening out the external surface of the sleeve; said process being characterized in that it comprises the following further steps subsequent to the rasping operation for spotting superficial defects on the outer layer of said sleeve:

operationally mounting said sleeve on a support means;

illuminating the surface of the outer layer of the sleeve with light at a low angle;

shooting the surface of the layer with at least one television camera to obtain at least one image of said surface, divided into a plurality of pixels distributed in an orderly fashion in horizontal rows and vertical rows intersecting one another;

reading the value of luminosity of the image at each pixel;

assigning to each pixel a first fictitious value of luminosity corresponding to the difference between the values of luminosity of at least two pixels contiguous with it, belonging to the horizontal rows contiguous with the horizontal row to which the pixel to which the first fictitious value is attributed respectively belongs;

discriminating the pixels whose first fictitious value is above a pre-set threshold level, from the pixels whose first fictitious value is below the threshold level;

assigning to each pixel a second fictitious value of luminosity, corresponding to the difference between the values of luminosity of at least two pixels contiguous with it, belonging to the vertical rows contiguous with the vertical row to which the pixel (P) to which the second fictitious value is attributed respectively belongs;

discriminating the pixels whose second fictitious value is above the pre-set threshold level, from the pixels whose second fictitious value is below said threshold level;

spotting the position of the superficial defects on the surface of the sleeve, on the basis of at least the vertical rows to which each of the pixels belongs in which at least one of said fictitious values is above the threshold level.

A further aspect of the invention is constituted by an apparatus for spotting superficial defects on the surface of sleeves of elastomeric material, characterized in that it comprises:

support means for operationally engaging a sleeve of elastomeric material;

at least one source of light arranged to illuminate the surface of the sleeve with light at a low angle;

at least one television camera arranged to shoot said surface to obtain at least one image divided into a plurality of pixels distributed in an orderly fashion in horizontal rows and vertical rows intersecting one another, each of said pixels being arranged to emit an electrical signal having a value proportional to the luminous intensity of the portion of image defined on it;

an electronic data processing unit operationally connected to the television camera for spotting the presence and the position of defects on said surface, by storing and processing the signals originating from the individual pixels.

Further characteristics and advantages will appear to a greater extent from the detailed description of a preferred but not exclusive embodiment of a process and an apparatus for spotting superficial imperfections on the surface of sleeves of elastomeric material, according to the present invention.

BRIEF DESCRIPTION OF THE DRAWINGS

Such description shall be made hereinafter with reference to the enclosed drawings, provided only as an indication and thus with no limiting intent, wherein:

FIG. 2 is an interrupted schematic view of the image of a portion of the surface of the sleeve, projected onto a grating of pixels emanating from a television camera provided in the machine;

FIG. 3a is a diagram which shows in its center square one of the pixels constituting the image of FIG. 2, together with the eight pixels nearby, taken into consideration with the object of assigning certain values of luminosity to the central pixel, said pixels being depicted together with their real values of luminosity;

FIG. 3b is a view similar to that of FIG. 3a, with reference to a pixel (arranged centrally) illuminated by the light reflected by a grinding crystal;

FIG. 4 represents a mask giving the multiplication factors attributed to each of the pixels of FIGS. 3a, 3b, to assign a value of weighted average to the pixel which is in the center in each said figures;

FIG. 4a shows the weighted average values of luminosity assigned to each of the pixels of FIG. 3a, after the processing operations executed with reference to the mask of FIG. 4;

FIG. 4b is a representation similar to FIG. 4a, executed with reference to FIG. 3b;

FIG. 5 represents a horizontal filtering mask giving the multiplication factors attributed to each of the pixels of FIGS. 3a, 3b, to assign to the pixel arranged centrally a first fictitious value of luminosity;

FIG. 5a represents the first fictitious values of luminosity assumed by the pixels of FIG. 4a, after the processing operation obtained with reference to the mask of FIG. 5;

FIG. 5b is a representation similar to that of FIG. 5a, executed with reference to the pixels of FIG. 4b;

FIG. 5c shows the image of the superficial portion of FIG. 2, after highlighting the pixels which, following the processing operation of FIGS. 4 and 5, have a value of luminosity above a pre-set threshold level;

FIG. 6 shows a vertical filtering mask, giving the multiplication factors adopted with reference to the pixels of FIGS. 4a, 4b, to assign a second fictitious value of luminosity to the pixel arranged centrally in said figures;

FIG. 6a shows the second fictitious values of luminosity assigned to the pixels of FIG. 4a, after the processing operation executed with reference to the vertical filtering mask of FIG. 6;

FIG. 6b is a representation similar to that of FIG. 6a, executed with reference to the pixels of FIG. 4b;

FIG. 6c represents the image obtained by highlighting the pixels which, after the processing operation by means of the vertical filtering mask, have a value of luminosity above a pre-set threshold level; and FIG. 7 shows a final image obtained by also highlighting, starting with FIG. 6c, the pixels which, after the processing operation with the mask of FIG. 4, have a value of luminosity above a pre-set threshold level.

Figure 1:
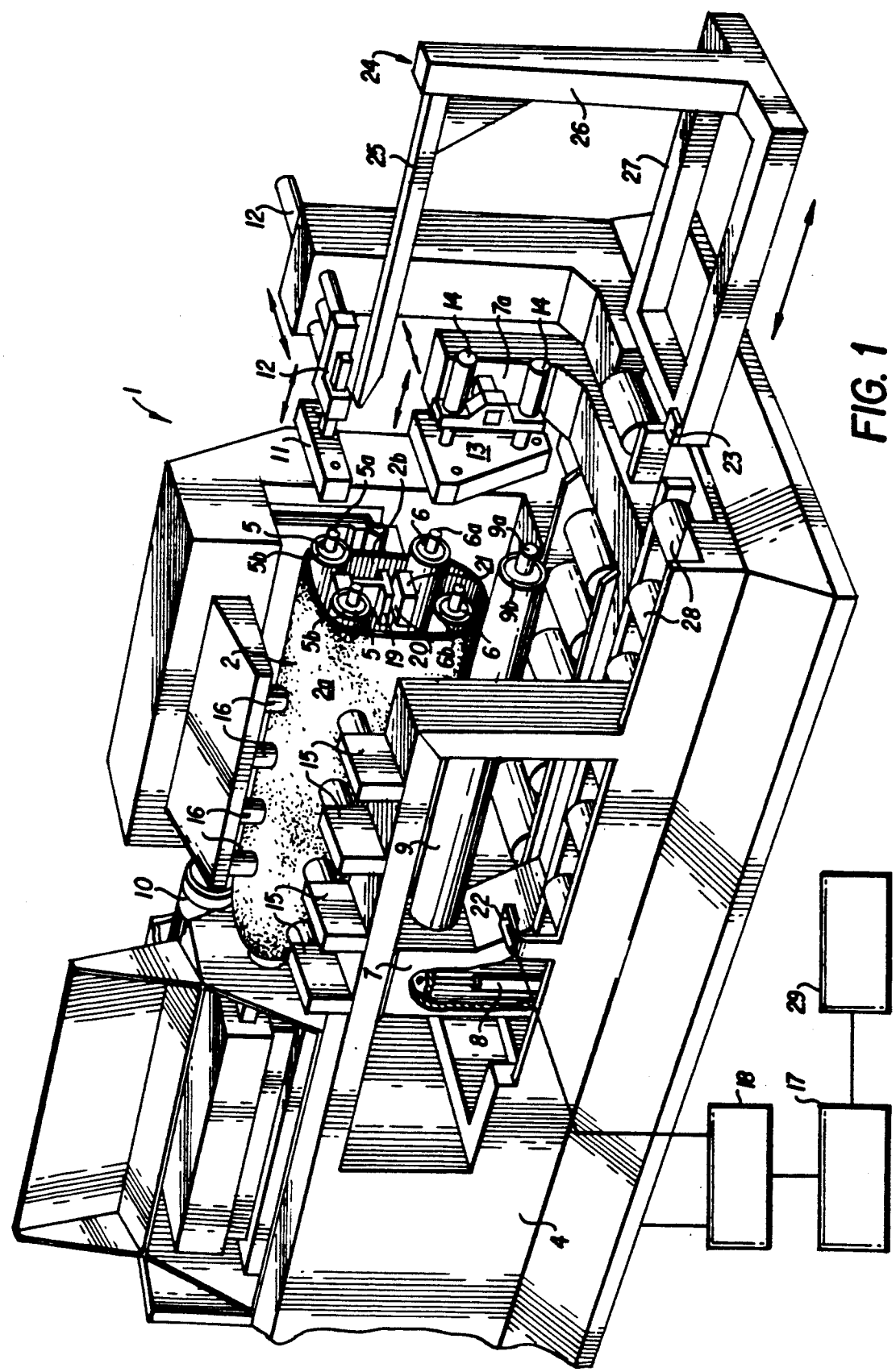
FIG. 1 is a perspective view of an apparatus used for actuating the subject process on sleeves of the type used for the manufacture of toothed belts.

With particular reference to FIG. 1, reference numeral 1 indicates as a whole a machine for spotting superficial defects on sleeves of elastomeric material, according to the present invention. The details of this machine are set forth in at least one of the copending applications listed above under the heading "Cross Reference to Related Applications".

In the illustrated embodiment, the machine 1 is ready to identify the presence of defects, if any, on the external surface 2a of a tubular sleeve 2 having internally a toothed surface 2b provided with a plurality of teeth extending longitudinally and at an equal distance from one another according to a pre-determined pitch.

The axially elongated sleeve 2 is destined to be subsequently cut at axially spaced locations along circumferential lines at an equal distance from one another, to obtain a plurality of toothed belts.

The machine 1 comprises essentially a base 4 on which means for support 5, 6, 9 are mounted to operationally sustain the sleeve 2.

In the embodiment illustrated the support means provides for at least one upper roller 5 rotatably engaged with the base 4 and at least one lower roller 6 parallel to the upper roller 5 and operationally engaged with a support column 7 movable, under the action of fluid-dynamic actuators 8 or similar means to allow the lower roller 6 to move closer to and away from the upper roller 5.

More in particular, in the illustrated embodiment there is provision for two upper rollers 5 and two lower rollers 6, arranged side by side and parallel to one another in substantially horizontal planes.

It also preferably to provide for the support column 7 to be connected to at least one auxiliary lower roller 9, arranged in a direction parallel to and under the lower rollers 6. The auxiliary roller 9 is used instead of the lower rollers 6 when the sleeves 2 being processed have a long circumferential extension.

With the means of support 5, 6, 9 there are associated means of movement, comprising a motor 10 operating on at least one of the upper rollers 5 so as to impart to the sleeve 2 a continuous rotary movement in a direction substantially perpendicular to the longitudinal extension of the teeth obtained on the internal surface 2a.

Each of the support rollers 5, 6, 9 has a coating layer of an elastomeric material 5b, 6b, 9b in order to ensure a positive grip on the toothed surface 2b and an easy adaptability to the different types of sleeve 2 being processed.

At least one of the extremities 5a of each upper roller 5 is adapted to be operationally engaged by a first removable support 11 moveable with two degrees of freedom and slidably guided with respect to the base 4 and laterally displaceable in the directions shown by the arrows, by fluid-dynamic cylinders 12 or such like, with respect to the upper rollers 5 to allow the engagement of the sleeve 2 around the same, as is clearly visible from FIG. 1.

In a similar manner, at least one of the extremities 6a, 9a of each of the lower roller 6 and of the auxiliary roller 9 is operationally engageable by a second removable support 13, connected to a lateral extension 7a of the support column 7 and laterally displaceable as shown by the arrows with respect to the lower rollers 6 and 9 by respective actuators 14.

The machine 1 also comprises one or more television cameras 15 operationally supported by the base 4 and operating in front of the external surface 2a of the sleeve 2, suitably illuminated with light at a low angle by at least one source of light 16, also operationally supported by the base 4.

In the illustrated embodiment there are four television cameras 15, equally spaced in a direction parallel to the longitudinal axis of the sleeve 2, and with each of which there is associated a source of light 16 placed above it.

For the object of the present invention, it is also possible to provide for only one television camera 15, possibly movable with respect to the sleeve 2 to explore the entire external surface 2a thereof.

As is clearly visible from FIG. 2, each of the television cameras 15 shoots a pre-determined portion of the external surface 2a obtaining, within a field of view Q having a pre-set extension, an image divided into a plurality of so-called "pixels" P distributed in an orderly fashion along horizontal lines H1 . . . H14 and vertical lines V1 . . . V14 which intersect one another.

Hereinafter the word "pixel" shall be meant to indicate, as is in any case known, a division of the image into squares or rectangles, with a size, say, of a square having a side of 0.5 mm and in any case having dimensions which depend on the type of camera and on the lens.

Each of the pixels P can be identified individually with respect to the others on the basis of the position occupied by it in the field of view Q. In particular, the position of each pixel P is identified by the horizontal rows H1 . . . H14 and vertical rows V1 . . . V14 to which the represent, in practice, the co-ordinates of the pixel P inside the field of view Q.

Still in a known manner in itself and thus not illustrated, with each pixel P there is associated a photo-receptor element which is ready to emit an electrical signal proportional to the intensity of the light impinging upon the pixel itself.

The television cameras 15 are directly connected (in a manner not illustrated in the figures) to an electronic data processing unit 17 which can in turn be connected to an electronic control unit 18, of the type commonly called a PLC, which controls the sequential operation of the different elements associated with the machine 1 (motor 10, actuating cylinders 8, 12, 14 and so on). The data processing unit 17, preferably being by a conventional "personal computer" which is connected, according to methods which shall be clarified later to a greater extent, to process the signals received by the individual pixels P for spotting the presence of any defects on the external surface 2a of the sleeve 2.

Within the scope of the operation of the machine 1, it is also possible to provide, to advantage, that the electronic data processing unit 17 be in a position to receive and process further signals originating from a laser-beam reading element 19, a photo-chromatic sensor 20, and an element for the emission and reception of supersonic waves 21, arranged respectively to verify the geometrical configuration of the toothed surface 2b, to check the joints of a coating material possibly applied to the toothed surface itself, and to identify the presence, if any, of structural cavities inside the sleeve 2.

The reading element 19, the photo-chromatic sensor 20 and the element for the emission and reception of supersonic waves 21 are not described further since they are not important for the object of the invention, and are in themselves discussed in detail in the several patent applications filed in the name of the same assignee already mentioned above in the section entitled "Cross Reference to Related Applications" and incorporated by reference herein.

It is provided for that in the memory of the data processing unit 17 there be introduced theoretical geometrical parameters corresponding to different types of sleeve 2 produced in the plant wherein the machine 1 is installed.

To each theoretical geometrical parameter of each type of sleeve 2 there is assigned an individual code which allows its immediate selective recall for the purpose of the execution of the operational steps of the machine 1.

The individual code corresponding to the sleeve 2 under test is read by the electronic control unit 18 when the sleeve itself is slipped onto the rollers 5, 6.

For this purpose, it is conventionally provided for that the electronic control unit 18 be used as a master of a magnetic reading and recording head 22 arranged to read information stored on a magnetic storage means, i.e. magnetic card 23 associated with a handling support 24 conventionally used to handle, among the different operating stations inside the plant, the sleeves 2 and the belts subsequently produced.

Such handling support 24 supports the sleeve 2 by means of a bar 25 fastened in a cantilever fashion to an upright 26 rising from a base frame 27.

The handling support 24 is positioned to be engaged operationally along a set of rollers 28 mounted in the lower part of the base 4 of the machine 1, to insert the sleeve 2 over the rollers 5, 6, arranged in a reciprocally close relationship with one another, simultaneously bringing the magnetic card 23 under the reading head 22.

In this situation, the electronic control unit 18 can transmit to the data processing unit 17 the individual code stored on the magnetic card 23 carried by the handling support 24.

The sleeve 2 is deposited onto the upper rollers 5, say, by lowering the set of rollers 28, after which the handling support 24 is slipped off the sleeve itself and moved to the right, as per FIG. 1, to provide space for the removable supports 11, 13 then to operationally engage with the extremities 5a, 6a, 9a of the upper rollers 5 and lower rollers 6, 9.

In the meantime, the data processing unit 17 has, in its memory, searched for the theoretical geometrical parameters corresponding to the individual code given to it by card 23. The data processing unit 17, through the electronic control unit 18, causes the lower rollers 6,9 to drop by an amount corresponding to the circumference of the particular sleeve delivered, so as to produce a certain tensioning of the sleeve 2.

At this point, the machine 1 starts the check of the external surface 2a of the sleeve 2 which, according to the subject process under examination, occurs according to the following procedure.

The data processing unit 17 enables the electronic control unit 18 to activate the motor 10 which, through the upper rollers 5, determines the rotary movement of the sleeve 2 in a direction perpendicular to its longitudinal extension.

In this situation, the television cameras 15 take a plurality of instantaneous shots of the surface 2a, according to pre-determined time intervals.

More accurately, the number of shots made by each television camera 15, as well as the time interval between one shot and the next, are regulated by the data processing unit 17 in relation to the external circumferential length of the sleeve itself and to the speed of movement imparted to it through the first support rollers 5 so that, by adding together the individual shots, the external surface 2a of the sleeve 2 is examined along its entire extension.

For each of the shots made by the television cameras 15, the signals emitted by the individual pixels P, initially of the analog type, are converted, in a known manner, into digital signals on the basis of which a classification is made of the different levels of luminosity which have determined the generation of the analog signals.

As an example, it is considered that to the signal originating from each pixel P it is possible to attribute any whole numerical value ranging from 0 to 256, of a magnitude proportional to the value of the analog signal.

More accurately, at the value 0 there is a total absence of illumination of the corresponding pixel P, while at the value 256 there is an illumination of the pixel P such as to bring to a state of saturation of the associated photo-receptor element.

The digital signals related to each of the shots taken are ready to be stored by the data processing unit 17 and, later, to be suitably processed to allow the identification of anomalies or defects, if any, present on the external surface 2a examined.

To advantage, the processing of the signals can be made directly by the data processing unit 17 during the course of the checks made by means of the reading element 19, the photo-chromatic sensor 20 and the element for the emission and reception of supersonic waves 21, or they may be transferrèd to a magnetic storage support to be processed in locations other than the location where the machine 1 is installed.

Preferably, the processing of the digital signals provides essentially that to each of the pixels P, there be assigned values of luminosity different from its real value of luminosity, obtained by mathematically interpolating the real values of luminosity of the pixel itself and of the pixels adjacent to it.

More in particular, as represented and as indicated in FIGS. 3a and 3b, within the scope of the processing each central pixel P' is examined while taking into consideration the eight pixels P which surround it, according to a quadrangular configuration.

In this respect, in the case of FIG. 3a the processing occurs with reference to a central pixel P on which there coincides the image of a horizontal edge of a fragment of paper "C" undesirably left on the surface 2a after the rasping operation. The paper fragment "C" in FIG. 2 is of parallelogram shape as shown in outline with the top edge along line H8 from V2 to V12 and its bottom edge along line H11 from V3 to V13.

Such pixel central P, as shown in FIGS. 2 and 3a, is identified by the intersection between the horizontal line H8 and the vertical line V9 of the field of view Q; that is, the central pixel P of FIG. 3A lies at the intersection of H8 and V9 which is within the border of the "C" parallelogram.

Inside each of the pixels P, as an indication, the values of luminosity related to them are given. As can easily be deduced, the pixels P having a level of luminosity 40 correspond to the dark surface of the elastomeric material corresponding to the sleeve, while the pixels P having a level of luminosity 110 correspond to the bright surface of the fragment of paper C.

In a substantially similar manner, in the case of the crystal K as illustrated in FIG. 3b the processing occurs with reference to a pixel P, corresponding to the intersection between the horizontal row H4 and the vertical row V3, strongly illuminated by the reflection of light due to a grinding crystal K present on the surface 2a. For the purposes of the test, it is necessary to arrange for this crystal to be ignored, since its presence causes no problem at all.

It is first of all provided for that to each pixel P there is assigned a value of weighted average luminosity. For this purpose, the pixels P considered according to what has been said with reference to FIGS. 3a, 3b are each multiplied by a certain factor, and the sum of the results obtained is divided by the number of pixels considered.

As can easily be deduced from the mask illustrated in FIG. 4, which gives the multiplication factors of the individual pixels P, each pixel P is multiplied by 1, so that the value of weighted average corresponds simply to the sum of the values of the real luminosity of the pixels P taken into consideration, divided by 9.

FIGS. 4a and 4b give the value of weighted average luminosity assigned to each of the pixels P of FIGS. 3a, 3b, adopting for each of them the criterion of calculation explained above.

As can easily be observed from FIG. 4b, following this processing operation, the value of the weighted average luminosity of the pixel P corresponding to the crystal K is equal to that assigned to the surrounding pixels P.

The processing operation of the signals also provides for the replacement of the value of weighted average luminosity of each pixel P with a first fictitious value of luminosity, corresponding to the difference between the values of luminosity of at least two pixels P contiguous with it, belonging to the horizontal rows H7, H9 and H3, H5, respectively, contiguous with the horizontal row H8, H4 to which the pixel belongs and to which such fictitious value is attributed. More accurately, the first fictitious value is obtained by adding together algebraically the value of weighted average of the pixels P considered in the FIGS. 4a, 4b, multiplied each by a certain factor, according to the representation of FIG. 5.

As can easily be observed from FIG. 5, the pixel P examined and the pixels P belonging to its horizontal row H8, H4 are multiplied by 0, while the pixels P belonging to each contiguous horizontal row H7, H9 and H3, H5 are multiplied by 1 and inverted as to sign with respect to those of the other contiguous horizontal row.

Looking at the results given in FIGS. 5a, 5b it is easy to deduce that, following such an operation, to the pixel P corresponding to the fragment of paper (FIG. 5a) there will be assigned a first fictitious value much higher than that assigned to the pixel corresponding to the crystal (FIG. 5b).

The processing operation continues with a step of discrimination of the pixels P whose first fictitious value is above a pre-determined threshold level, from the pixels whose first fictitious value is, on the other hand, below such threshold level.

If, say, 90 is selected as the threshold level, the central pixel P in FIG. 5a would have the first fictitious value above such threshold level, and would be discriminated by the central pixel P of FIG. 5b. It should be noted that the only pixels P which have the first fictitious value above the threshold level, will be those coincident with or at least close to the horizontal edges of the fragment of paper C or of other structural imperfections such as a cut or a protrusion.

In actual fact, for the pixels P corresponding to the central areas of the fragment of paper C and/or to its vertical edges, first fictitious values will be obtained which are below the threshold level.

As a result of the discrimination mentioned above, it will be possible to obtain, by highlighting the pixels P having a first fictitious value above the threshold level, a new portrayal of the field of view according to the representation of FIG. 5c.

In a processing step distinct from that which leads to the assignment of the first fictitious value, the average weighted value of each pixel P is replaced by a second fictitious value of luminosity, corresponding to the difference between the values of luminosity of at least two pixels P contiguous with it, belonging to vertical rows respectively contiguous with the vertical row to which the pixel P belongs and to which said second fictitious value is attributed.

More in particular, the algebraic addition is made of the results obtained by multiplying the average weighted value of each of the pixels P considered with reference to FIGS. 4a, 4b, by a certain factor, according to the diagram in the mask of FIG. 6. As can easily be observed, while the pixels P belonging to the vertical row V9, V3 arranged centrally are multiplied by 0, the pixels P belonging to the vertical rows V8, V10 and V2, V4 to the side are multiplied by 1, with respectively inverted signs.

In a manner similar to what has emerged from the considerations made with reference to the assignment of the first fictitious value, the second fictitious value will be above the threshold level mentioned earlier only with reference to those pixels P belonging to the vertical edges of a fragment of paper or of another superficial defect.

The second fictitious values of the pixels P corresponding to the horizontal edges of the defects or of the pixels P corresponding to the crystals shall, on the other hand, be much smaller, and in any case below the threshold level.

Progress is then made to the discrimination of the pixels P with a second fictitious value above the threshold level from the pixels P whose second fictitious value has, on the other hand, a value below such level.

If we now take into consideration the pixels P having a second fictitious value above the threshold level, together with the pixels P previously highlighted, it is possible to obtain a representation of the field of view according to what can be seen in FIG. 6c, where the entire contour of the fragment of paper 6 is highlighted.

At this point it is also possible to highlight the internal regions of the small piece of paper or other type of defect, taking into considerations the pixels P which, before the assignment of the first and of the second fictitious value, had weighted average value above the threshold level.

There is thus obtained a graphical representation of the appearance of the surface 2a in the field of view Q taken by the television camera 15.

As it is easy to see from FIG. 7, the crystal K visible in FIG. 2 is absent from this representation.

On the basis of at least the position of the vertical rows of the pixels P having fictitious values of luminosity above the threshold level, as well as on the position of the television camera 15 which has taken the shot, it is possible to establish the exact position occupied by the defect along the longitudinal extension of the sleeve and, thus, to establish which of the belts that will be obtained following the cutting up of the sleeve will have said defect.

In the case wherein the data processing operation described above is executed directly by the data processing unit 17, the position of the defects can be stored by the data processing unit itself.

When, at the end of the test, the handling support 24 is once again engaged on the set of rollers 28 to withdraw the sleeve 2, the data processing unit 17 will send onto the magnetic card 23, through the electronic control unit 18 and the reading and recording head 22, signals related to the position of the detected superficial defects.

The signals introduced onto the magnetic card 23 allows other automatic machines, provided for in the production cycle of the belts, to identify and reject the belts which after the subsequent cutting operation of the sleeve 2, will have the detected defects.

The process of the present invention also allows a timely intervention to eliminate the causes which have occasioned the formation of the superficial defects.

For this purpose, it is provided for that the data processing unit 17 be in a position of transmitting to a central processing unit 29 the data taken during the course of the test. The central processing unit 29, which supervises the operation of the main units used in the production cycle of the belts, signals the operating anomaly of the unit or units wherein it is presumed that the formation of the superficial defects has originated.

As an alternative to the above description it is possible to so provide that it is the electronic control unit 18 to transmits to the central processing unit 29 the data taken during the course of the test.

With the process and the machine under examination it is possible to obtain in an entirely automatic way an objective assessment, and thus one that is extremely effective and reliable, of the presence of possible superficial defects on sleeves and such like.

The risk is thus avoided of sending belts to the user which contain unseen defects as it was possible to occur in the past when examination was only with the naked eye.

With the method of the invention it is also possible to avoid any delay in the detection of the defects as was possible to occur in the past when the examination with the naked eye was extended to ascertaining both the defects internal to the sleeve and the external ones.

According to the present method it is in fact possible to shoot with the television camera 15 the entire surface of the sleeve and then to reproduce the image in a manner independent of the machine of FIG. 1 kept active so as to execute on the sleeve further checking steps such as, say, on the internal portion to ascertain the geometrical regularity of the teeth of the belts; see the aforementioned "Cross Reference to Related Applications".

By operating in this way the internal checking steps of the sleeve are not delayed by any longer time than is needed for checking the sleeve's surface irregularities; in particular, it is possible to obtain a simultaneously a check of the two types of defects, thus with clearly lesser time needed for the verification of each sleeve and consequent immediate intervention to restore optimum process parameters during the belts' manufacture.

Attention is drawn to the fact that the methods adopted in the described process and machine allow to advantage, in spite of the identification of defects by means of television cameras 15, to exclude any chance that possible crystals deposited on the sleeve during the grinding step or any particles of dust in any part whatsoever, having a high degree of reflection, shall be erroneously recognized as defects.

Naturally, to the invention thus conceived, numerous modifications and variants may be made, all falling within the scope of the inventive concept which characterize it as defined by the following claims.

We claim:

1. A process for locating superficial defects on a layer of elastomeric material, comprising the following steps:
   mounting said layer on a support means;
   illuminating the surface of the layer with light at a low angle;
   shooting the surface of the layer with at least one television camera to obtain at least one image of said surface, which is divided into a plurality of pixels distributed in an orderly fashion in horizontal rows and vertical rows intersecting one another;
   reading the value of luminosity of the image at each pixel;
   assigning to each pixel a first fictitious value of luminosity corresponding to the difference between the values of luminosity of at least two pixels contiguous with it, belonging to the horizontal rows on each side of the horizontal row in which the pixel to which the first fictitious value is attributed is located;
   discriminating the pixels having a first fictitious value above a pre-set threshold level from the pixels whose first fictitious value is below the threshold level;
   assigning to each pixel a second fictitious value of luminosity, corresponding to the difference between the values of luminosity of at least two pixels contiguous with it, belonging to vertical rows on each side of the vertical row to which the pixel to which the second fictitious value is attributed is located;
   discriminating the pixels having a second fictitious value is above the pre-set threshold level, from the pixels whose second fictitious value is below said threshold level;
   locating the position of any superficial defects on the sleeve, on the basis of at least the vertical rows to which each of the pixels belongs wherein at least one of said fictitious values is above the threshold level.

2. A process according to claim 1 in which prior to the assignment of the first fictitious value, the assignment is made, to each of said pixels, of a value of weighted average of luminosity, corresponding to the sum of the values of luminosity of the same pixel and of the pixels adjacent to it, divided by the number of values of luminosity added together.

3. A process according to claim 1 in which the first fictitious value of luminosity is assigned to each pixel considering, for each of the horizontal rows contiguous with the horizontal row to which the same pixel belongs, the sum of the values of three pixels contiguous with the pixel to which the first fictitious value is assigned.

4. A process according to claim 1 in which the second fictitious value of luminosity is assigned to each pixel considering, for each of the vertical rows contiguous with the vertical row to which the same pixel belongs, the sum of the values of three pixels contiguous with the pixel to which the second fictitious value is assigned.

5. A process according to claim 1 in which after the steps of discrimination, performing a step of highlighting the pixels having at least one of said fictitious values above the threshold level.

6. A process according to claim 5 in which during said highlighting step those pixels are also highlighted which, after said detection step, have values of luminosity above said threshold level.

7. A process according to claim 2 in which the assignment of the value of weighted average to each pixel, is made considering the value of luminosity of the same pixel and the values of luminosity of eight pixels arranged according to a quadrangular configuration around the pixel to which the value of weighted average is assigned.

8. A machine for locating superficial defects on a layer of elastomeric material comprising:
   support means for operationally engaging a layer of elastomeric material;
   at least one source of light arranged to illuminate a surface of the elastomeric material with light at a low angle;
   at least one television camera position to shoot said surface of the layer to obtain at least one image divided into a plurality of pixels distributed in an orderly fashion in horizontal rows and vertical rows and intersecting one another, each of said pixels being arranged to emit an electrical signal having a value proportional to the luminous intensity of the portion of image defined on it;
   an electronic data processing unit operationally connected to the television camera for spotting the presence and the position of defects on said surface, by storing and processing the signals originating form the individual pixels;
   a magnetic reading and recording head operationally connected to said electronic data processing unit to transmit to said unit an individual code stored on a magnetic storage means associated with a handling support which moves the elastomeric material, wherein geometrical parameters of several elastomeric materials are stored in said electronic data processing unit which can be recalled selectively by means of said individual code;
   said data processing unit comprising means to record on the magnetic storage means, by means of the magnetic reading and recording head, the position along the longitudinal extension of the elastomeric surface of said defects.

9. A machine according to claim 8 further comprising a plurality of television cameras, each of which executes a shot on a pre-determined portion along the extension of said surface.

10. A machine according to claim 9 further comprising a plurality of light sources each associated with one of said television cameras.

11. A machine according to claim 8 further comprising movement means for imparting to the elastomeric layer a movement in a direction transverse to its longitudinal extension, said at least one television camera being positioned to take a plurality of instantaneous shots each corresponding to a pre-determined portion of the extension of said surface.

12. A machine according to claim 10 in which said support means comprises, for layers in the form of sleeves, at least one upper support roller and at least one lower support roller parallel to one another and mounted for movement closer to and further away from one another to operationally engage the sleeve to impart a pre-determined tensioning to said sleeve.

13. A machine according to claim 12 in which each support roller has a layer of coating of elastomeric material.

14. A machine according to claim 10 said support means further comprising a pair of upper rollers and a pair of lower rollers positioned side by side and parallel to one another according to respective horizontal planes.

15. A machine according to claim 12 further comprising at least one auxiliary lower roller, positioned below said lower roller.

16. A machine according to claim 12 in which said lower support roller is operationally engaged with a support column movable by actuating means to allow the lower roller to move closer to and away from the upper roller.

17. A machine according to claim 12 in which each of said upper rollers and lower rollers has one of its extremities operationally sustained by a removable support which is mounted to be laterally displaceable with respect to the corresponding roller to allow the engagement of a tubular sleeve on said upper and lower rollers.

18. A machine according to claim 8 in which said electronic data processing unit is operationally connected to a central data processor to transmit to the process the presence of any defects on the surface of the sleeve, said central data processor being arranged to signal the presence of data indicating operating anomalies on machines which were used earlier in the production of the sleeve.

19. A process for spotting superficial defects on the outer layer of a sleeve of a transmission belt of elastomeric material, said defects comprising cuts, cracks or grooves due to the curing cycle and further defects including residues from previous manufacturing steps, said process comprising the following steps:
    mounting said sleeve on support means;
    illuminating the surface of the outer layer of the sleeve with light at a low angle;
    shooting the surface of the layer with at least one television camera to obtain at least one image of said surface, which is divided into a plurality of pixels distributed in an orderly fashion in horizontal rows and vertical rows intersecting one another;
    reading the value of luminosity of the image at each pixel;
    assigning to each pixel a first fictitious value of luminosity corresponding to the difference between the values of luminosity of at least two pixels contiguous with it, belonging to the horizontal rows on each side of the horizontal row to which the pixel to which the first fictitious value is attributed respectively belongs;
    discriminating the pixels having a first fictitious value above a pre-set threshold level from the pixels whose first fictitious value is below the threshold level;
    assigning to each pixel a second fictitious value of luminosity, corresponding to the difference between the values of luminosity of at least two pixels contiguous with it, belonging to vertical rows on each side of the vertical row to which the pixel to which the second fictitious value is attributed is located;
    discriminating the pixels having a second fictitious value which is above the pre-set threshold level, from the pixels whose second fictitious value is below said threshold level;
    locating the position of any superficial defects on the sleeve, on the basis of at least the vertical rows to which each of the pixels belongs wherein at least one of said fictitious values is above the threshold level.

20. A process for the manufacture of transmission belts comprising an annular body of elastomeric material incorporating at least one layer of longitudinal reinforcing cords arranged side by side, said process comprising the steps of:
    winding in succession on a cylindrical matrix at least one layer of elastomeric material combined with at least one layer of inextensible cords which is wound circumferentially onto said matrix to form a sleeve;
    coating the outer layer of the sleeve thus obtained with a sheet of paper or such like;
    engaging on the layer of paper coating a rubber sheath and curing the sleeve by exerting a combined action of heating and centripetal pressure by means of fluid under pressure applied to the outside of the rubber sheath;
    extracting the sleeve from the sheath at the end of the curing operation;
    rasping the external surface of the sleeve to remove said sheet of paper and evening out the external surface of the sleeve;
    said process comprising the following further steps subsequent to the rasping operation and for spotting superficial defects on the outer layer of said sleeve:
    mounting said sleeve on a support means;
    illuminating the surface of the outer layer of the sleeve with light at a low angle;
    shooting the surface of the layer with at least one television camera to obtain at least one image of said surface, which is divided into a plurality of pixels distributed in an orderly fashion in horizontal rows and vertical rows intersecting one another;
    reading the value of luminosity of the image at each pixel;
    assigning to each pixel a first fictitious value of luminosity corresponding to the difference between the values of luminosity of at least two pixels contiguous to it and belonging to the horizontal rows on each side of the horizontal row to which the pixel to which the first fictitious value is attributed is located;

discriminating the pixels having a first fictitious value is above a pre-set threshold level, from the pixels having a first fictitious value which is below the threshold level;

assigning to each pixel a second fictitious value of luminosity, corresponding to the difference between the values of luminosity of at least two pixels contiguous to it and belonging to the vertical rows on each side of the vertical row to which the pixel to which the second fictitious value is attributed is located;

discriminating the pixels whose second fictitious value is above the pre-set threshold level, from the pixels having a second fictitious value which is below said threshold level;

locating the position of the superficial defects on the sleeve, on the basis of at least the vertical rows to which each of the pixels belongs in which at least one of said fictitious values is above the threshold level.

21. A machine according to claim 8 wherein said elastomeric material is an external surface of a tubular sleeve destined to be cut by means for cutting said tubular sleeve at axially spaced locations along circumferential lines of said tubular sleeve at equal distances from one another so as to obtain a plurality of transmission belts.

* * * * *